(12) United States Patent
Mah

(10) Patent No.: US 9,114,494 B1
(45) Date of Patent: Aug. 25, 2015

(54) ELECTRONIC DRILL GUIDE

(71) Applicant: Kenneth Jack Mah, Edmonton (CA)

(72) Inventor: Kenneth Jack Mah, Edmonton (CA)

( * ) Notice: Subject to any disclaimer, the term of this patent is extended or adjusted under 35 U.S.C. 154(b) by 217 days.

(21) Appl. No.: 13/828,898

(22) Filed: Mar. 14, 2013

(51) Int. Cl.
| | |
|---|---|
| A63B 69/36 | (2006.01) |
| B23Q 17/24 | (2006.01) |
| B23B 49/00 | (2006.01) |
| B23Q 17/22 | (2006.01) |
| B27G 23/00 | (2006.01) |
| G01D 21/00 | (2006.01) |
| B25H 1/00 | (2006.01) |
| A61B 17/00 | (2006.01) |
| B25C 7/00 | (2006.01) |
| G01B 11/26 | (2006.01) |
| A63B 53/04 | (2015.01) |

(52) U.S. Cl.
CPC ........ B23Q 17/2233 (2013.01); B23Q 17/2414 (2013.01); *A61B 2017/00725* (2013.01); *A63B 53/0487* (2013.01); *A63B 69/3685* (2013.01); *B23Q 17/2225* (2013.01); *B23Q 17/24* (2013.01); *B25C 7/00* (2013.01); *B25H 1/0092* (2013.01); *G01B 11/26* (2013.01)

(58) Field of Classification Search
CPC ........... A63B 69/3685; A63B 53/0487; B25H 1/0092; B23Q 17/24; B23Q 17/2225; G01B 11/26; B25C 7/00; A61B 2017/00725
USPC .................................................. 33/263, 626
See application file for complete search history.

(56) References Cited

U.S. PATENT DOCUMENTS

| | | | |
|---|---|---|---|
| 1,234,594 | A | 7/1917 | Wilner |
| 2,822,615 | A | 2/1958 | Durst et al. |
| 3,052,036 | A | 9/1962 | Oliver |
| 4,141,151 | A | 2/1979 | Jansky |
| 4,154,001 | A | 5/1979 | Serafin |
| 4,179,231 | A | 12/1979 | Hadden |
| 4,295,279 | A | 10/1981 | Sienknecht |
| 4,393,599 | A | 7/1983 | Sterrenberg |
| 4,457,078 | A | 7/1984 | Suchy |
| 4,765,786 | A | 8/1988 | Krogh |
| 5,130,658 | A * | 7/1992 | Bohmer ........................ 324/435 |
| 6,247,879 | B1 | 6/2001 | Costa |
| 6,375,395 | B1 | 4/2002 | Heintzeman |
| 6,499,219 | B1 | 12/2002 | Wightman |
| 6,587,184 | B2 | 7/2003 | Wursch et al. |

(Continued)

FOREIGN PATENT DOCUMENTS

DE          4336730 A1 *   5/1995

OTHER PUBLICATIONS

Lee Valley Tools Ltd., Woodworking Catalog, Sep. 2012, p. 40, Ogdensburg, NY, USA.

*Primary Examiner* — Laura Martin
*Assistant Examiner* — Rhyan C Lange

(57) ABSTRACT

One embodiment of an alignment apparatus for aligning an object, such as a tool or other implement, perpendicular with respect to a horizontal or a vertical target surface, comprises a three-axis accelerometer and at least two forward-facing distance sensors and a projection display comprising four addressable laser projectors. The accelerometer and distance sensor outputs are mapped to a predefined graphic symbol representing the orientation of the tool relative to the target surface, in particular when the tool is perpendicular to the target surface. The projection display projects the predefined symbol onto the target surface where it may be easily viewed by the tool operator allowing the operator to make any necessary corrections to the tool position.

11 Claims, 15 Drawing Sheets

(56) References Cited

U.S. PATENT DOCUMENTS

| | | |
|---|---|---|
| 6,878,954 B2 | 4/2005 | Butler et al. |
| 6,898,860 B2 | 5/2005 | Wu |
| 7,083,366 B2 | 8/2006 | Tung |
| 7,146,739 B2 * | 12/2006 | Ku et al. ............ 33/286 |
| 7,154,406 B1 | 12/2006 | Judge |
| 7,200,516 B1 * | 4/2007 | Cowley ............ 702/151 |
| 7,375,361 B2 * | 5/2008 | Turner et al. ............ 250/559.3 |
| 7,447,565 B2 | 11/2008 | Cerwin |
| 7,874,077 B2 | 1/2011 | Borinato |
| 7,992,311 B2 | 8/2011 | Cerwin |
| 2004/0216314 A1 | 11/2004 | Ch Fung et al. |
| 2004/0252293 A1 | 12/2004 | Laver et al. |
| 2005/0251294 A1 * | 11/2005 | Cerwin ............ 700/279 |
| 2009/0165313 A1 * | 7/2009 | Borinato ............ 33/263 |
| 2012/0163932 A1 * | 6/2012 | Schmidt et al. ............ 408/1 R |
| 2014/0000921 A1 * | 1/2014 | Vanko et al. ............ 173/11 |
| 2014/0007442 A1 * | 1/2014 | Pettersson et al. ............ 33/626 |

* cited by examiner

ELECTRONIC DRILL GUIDE

CROSS-REFERENCE TO RELATED APPLICATIONS

This application claims the benefit of provisional patent application Ser. No. 61/678,868 filed 2012 Aug. 2 by the present inventor.

BACKGROUND

Prior Art

The following is a tabulation of some prior art that presently appears relevant:

| U.S. Patents | | | |
|---|---|---|---|
| U.S. Pat. No. | Kind Code | Issue Date | Patentee |
| 1,234,594 | A | 1917-07-24 | Wilner |
| 2,822,615 | A | 1958-02-11 | Durst et al. |
| 3,052,036 | A | 1962-09-04 | Oliver |
| 4,141,151 | A | 1979-02-27 | Jansky |
| 4,154,001 | A | 1979-05-15 | Serafin |
| 4,179,231 | A | 1979-12-18 | Hadden |
| 4,295,279 | A | 1981-10-20 | Sienknecht |
| 4,393,599 | A | 1983-07-19 | Sterrenberg |
| 4,457,078 | A | 1984-07-03 | Suchy |
| 4,765,786 | A | 1988-07-23 | Krogh |
| 6,247,879 | B1 | 2001-06-19 | Costa |
| 6,375,395 | B1 | 2002-04-23 | Heintzeman |
| 6,499,219 | B1 | 2002-12-31 | Wightman |
| 6,587,184 | B2 | 2003-07-01 | Wursch et al. |
| 6,878,954 | B2 | 2005-04-12 | Butler et al. |
| 6,898,860 | B2 | 2005-05-31 | Wu |
| 7,154,406 | B1 | 2006-12-26 | Judge |
| 7,200,516 | B1 | 2007-04-03 | Cowley |
| 7,874,077 | B2 | 2011-01-25 | Borinato |
| 7,992,311 | B2 | 2011-08-09 | Cerwin |

| U.S. patent application publications | | | |
|---|---|---|---|
| Publication Nr. | Kind Code | Publication Date | Applicant |
| 2004/0216314 | A1 | 2004-11-04 | Ch Fung et al. |
| 2004/0252293 | A1 | 2004-12-16 | Laver et al. |

The present invention relates to a guide which assists a drill operator with the orientation of a hand-held power drill. It is often desirable or necessary to drill a perpendicular hole with a hand-held power drill. In practice, it is very difficult to consistently drill perpendicular holes using a hand-held power drill, particularly when the operator cannot stand directly behind the drill such as when the operator is reaching overhead.

The use of drill guides is known in the prior art. Existing solutions rely on mechanical jigs such as U.S. Pat. No. 4,765,786 to Krogh (1988) and U.S. Pat. No. 4,179,231 to Hadden (1979). Mechanical jigs are cumbersome and sometimes even dangerous to use. Such jigs are typically temporarily installed on the target surface which hinders visibility of the surface.

Various solutions using bubble levels exist such as U.S. Pat. No. 4,141,151 to Jansky (1979) and U.S. Pat. No. 6,499,219 B1 to Wightman (2002). Bubble levels work well when drilling into horizontal surfaces but it can be burdensome to view and position the small bubble between the lines. Bubble levels do not provide a full solution when drilling into vertical target surfaces such as a wall. When drilling a vertical surface, the bubble level can only help the drill operator align the drill perpendicular to the wall in the vertical axis i.e., it can only determine the inclination of the tool from the true horizontal direction. The bubble level and other gravity-based solutions such as U.S. Pat. No. 7,154,406 B1 to Judge (2006) and U.S. Pat. No. 7,874,077 B2 to Borinato (2011) do not help the operator align the drill perpendicular to the wall in the horizontal axis. When drilling into a vertical surface, gravity-based solutions cannot detect when the drill is tilted to the left or right of center.

Other solutions such as U.S. Pat. No. 7,200,516 B1 to Cowley (2007) and U.S. Patent Application Publication No. US 2004/0252293 A1 to layer et al. (2004) describe an alignment apparatus which projects several visible alignment dots onto the target surface. The operator is expected to visually estimate the size of the dots or the spacing between the dots in order to determine alignment.

The solutions known up to the present time suffer from a variety of disadvantages:
(a) A physical jig uses moving parts such as bearings or sliders which will require maintenance.
(b) A physical jig hinders visibility of the target surface.
(c) Bubble or spirit levels are small and often hard-to-read. They can be impractical to read if the drill is being used overhead.
(d) Gravity-based solutions such as a bubble level or a pendulum only work well on horizontal target surfaces.
(e) When dealing with a vertical target surface, gravity-based solutions such as a bubble level or a pendulum only help to align the drill inclination.
(f) Solutions based on projected alignment dots rely on the operator's visual skill in estimating size and spacing.

SUMMARY

In accordance with one embodiment, an electronic drill guide for a hand-held power drill comprises a three-axis accelerometer, at least two forward-facing distance sensors, and a projection display. The drill orientation relative to the target surface is mapped to one of several predetermined drill orientation symbols. The projection display projects the orientation symbol directly onto the target surface where it may be easily viewed by the drill operator allowing the operator to make any necessary corrections to the tool position.

Advantages

Accordingly several advantages of one or more aspects are as follows: 1) no mechanical jigs are required, increasing safety and convenience; 2) the operator is able to use the device to help position a drill truly perpendicular, in two axes, not merely inclination, to a vertical target surface; 3) the device is easy to read since the drill orientation status is projected directly onto the target surface; 4) the drill orientation symbols provide the drill operator with unambiguous notification of when the drill orientation is perpendicular to the target surface, allowing consistent and repeatable operation regardless of the tool operator's judgment or skill. These and other advantages of one or more aspects will become apparent from a consideration of the ensuing description and accompanying drawings.

DRAWINGS

Figures

In the drawings, closely related figures have the same number but different alphabetic suffixes.

FIGS. 12A-12J show orientation symbols of one embodiment.

Figure 12A:
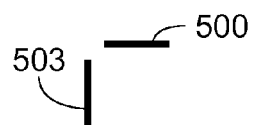
Figure 12B:
Figure 12C:
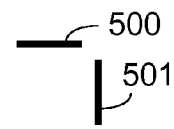
Figure 12D:
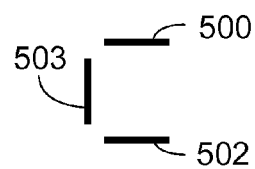
Figure 12E:
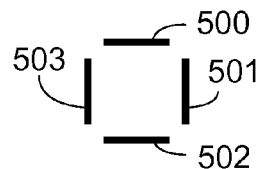
Figure 12F:
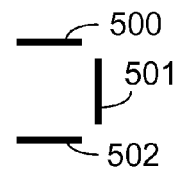
Figure 12G:
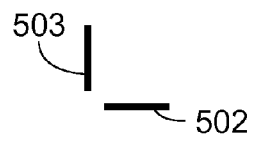
Figure 12H:
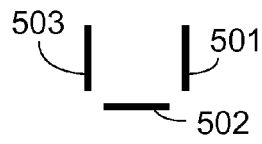
Figure 12J:
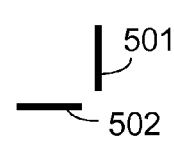

FIG. 12A is a symbol representing "upper-left."
FIG. 12B is a symbol representing "up."
FIG. 12C is a symbol representing "upper-right."
FIG. 12D is a symbol representing "left."
FIG. 12E is a symbol representing "perpendicular."
FIG. 12F is a symbol representing "right."
FIG. 12G is a symbol representing "lower-left."
FIG. 12H is a symbol representing "down."
FIG. 12J is a symbol representing "lower-right."

FIGS. 13A-13J show orientation symbols of an alternate embodiment.

Figure 13A:
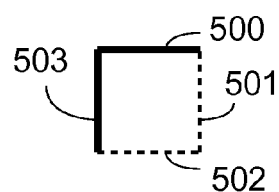
Figure 13B:
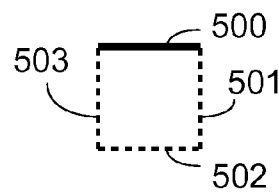
Figure 13C:
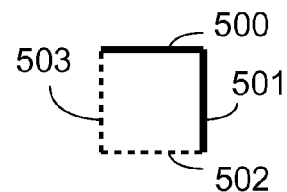
Figure 13D:
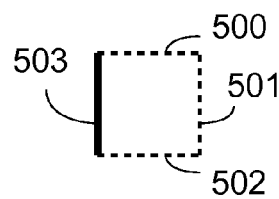
Figure 13E:
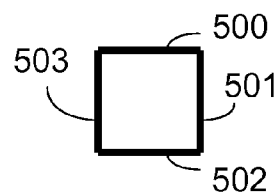
Figure 13F:
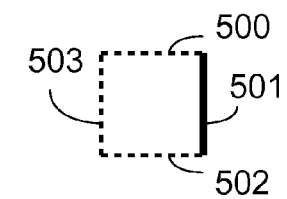
Figure 13G:
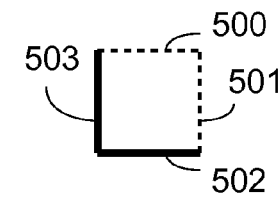
Figure 13H:
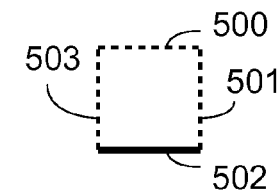
Figure 13J:
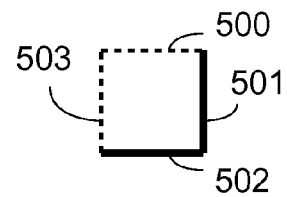

FIG. 13A is a symbol representing "upper-left."
FIG. 13B is a symbol representing "up."
FIG. 13C is a symbol representing "upper-right."
FIG. 13D is a symbol representing "left."
FIG. 13E is a symbol representing "perpendicular."
FIG. 13F is a symbol representing "right."
FIG. 13G is a symbol representing "lower-left."
FIG. 13H is a symbol representing "down."
FIG. 13J is a symbol representing "lower-right."

FIGS. 14A-14J show orientation symbols of an alternate embodiment.

Figure 14A:
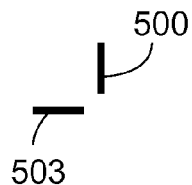
Figure 14B:
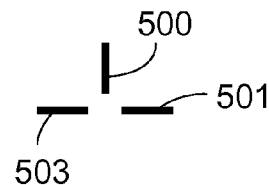
Figure 14C:
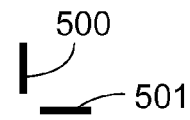
Figure 14D:
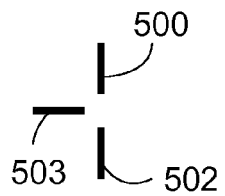
Figure 14E:
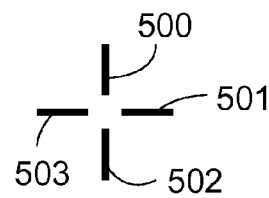
Figure 14F:
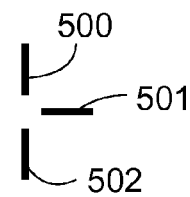
Figure 14G:
Figure 14H:
Figure 14J:
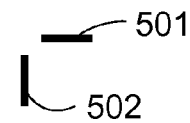

FIG. 14A is a symbol representing "upper-left."
FIG. 14B is a symbol representing "up."
FIG. 14C is a symbol representing "upper-right."
FIG. 14D is a symbol representing "left."
FIG. 14E is a symbol representing "perpendicular."
FIG. 14F is a symbol representing "right."
FIG. 14G is a symbol representing "lower-left."
FIG. 14H is a symbol representing "down."
FIG. 14J is a symbol representing "lower-right."

FIGS. 15A-15J show orientation symbols of an alternate embodiment.

Figure 15A:
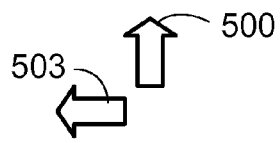
Figure 15B:
Figure 15C:
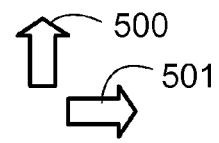
Figure 15D:
Figure 15E:
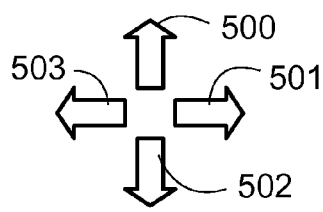
Figure 15F:
Figure 15G:
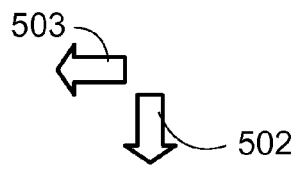
Figure 15H:
Figure 15J:
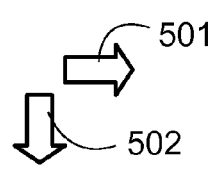

FIG. 15A is a symbol representing "upper-left."
FIG. 15B is a symbol representing "up."
FIG. 15C is a symbol representing "upper-right."
FIG. 15D is a symbol representing "left."
FIG. 15E is a symbol representing "perpendicular."
FIG. 15F is a symbol representing "right."
FIG. 15G is a symbol representing "lower-left."
FIG. 15H is a symbol representing "down."
FIG. 15J is a symbol representing "lower-right."

DRAWINGS

Reference Numerals 30 enclosure
31 gap
32 handle
33 switch
34 threaded bolt
40 collar
51 distance "L"
52 distance "R"
53 drilling axis
54 target surface
60 power drill
61 drill bit
64 trigger
65 battery pack
100R (right) distance sensor module
100L (left) distance sensor module
101X (x-axis) accelerometer
101Y (y-axis) accelerometer
101Z (z-axis) accelerometer
102 difference amplifier circuit
201 low-pass filter
202 low-pass filter
203 analog switch
204 summer circuit
205 H-signal (horizontal)
206 noise generator
210 comparator circuit
211 comparator circuit
212 window comparator circuit
301 low-pass filter
302 low-pass filter
303 analog switch
304 summer circuit
305 V-signal (vertical)
310 comparator circuit
311 comparator circuit
312 window comparator circuit
330 AND gate
331 retriggerable monostable multivibrator
341 amplifier circuit
342 bar-graph module
400R (right) projector
400L (left) projector
400T (top) projector
400B (bottom) projector
400C (center) projector
410 bar-graph display
420 audible alert device
421 motor driver
422 vibrator motor
430 microcontroller
431 display
500 ("pointed up") orientation symbol element
501 ("pointed right") orientation symbol element
502 ("pointed down") orientation symbol element
503 ("pointed left") orientation symbol element

DETAILED DESCRIPTION

First Embodiment—FIGS. 1, 2, 7-9, 12A-12J

The following description is not to be taken in a limiting sense, but is made merely for the purpose of describing the general principles of the electronic drill guide. The scope of the drill guide should be determined with reference to the claims.

Figure 1:
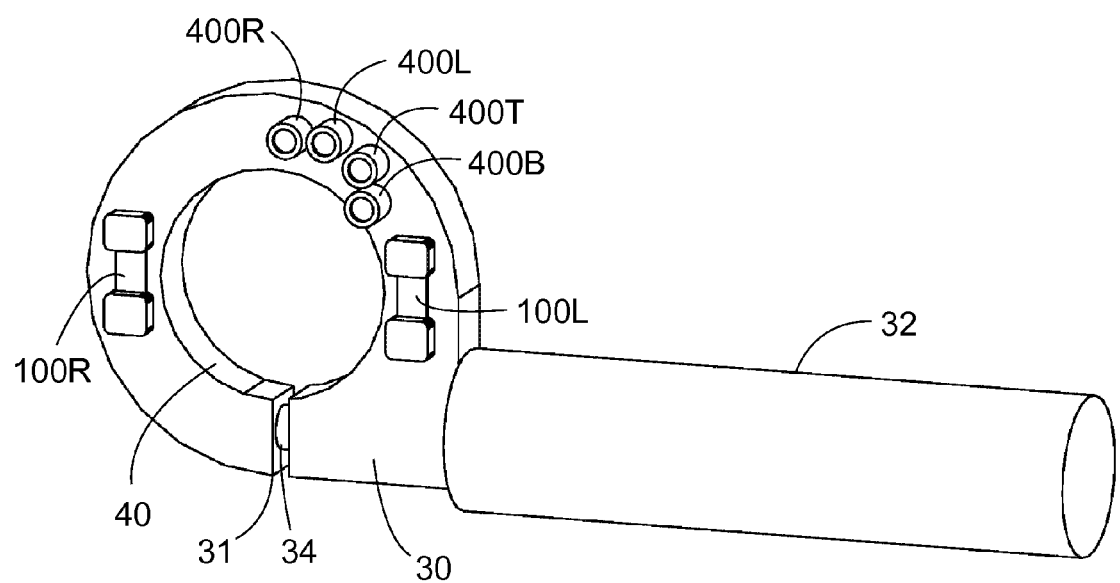
FIG. 1 shows a perspective front view of the first embodiment.
Figure 2:
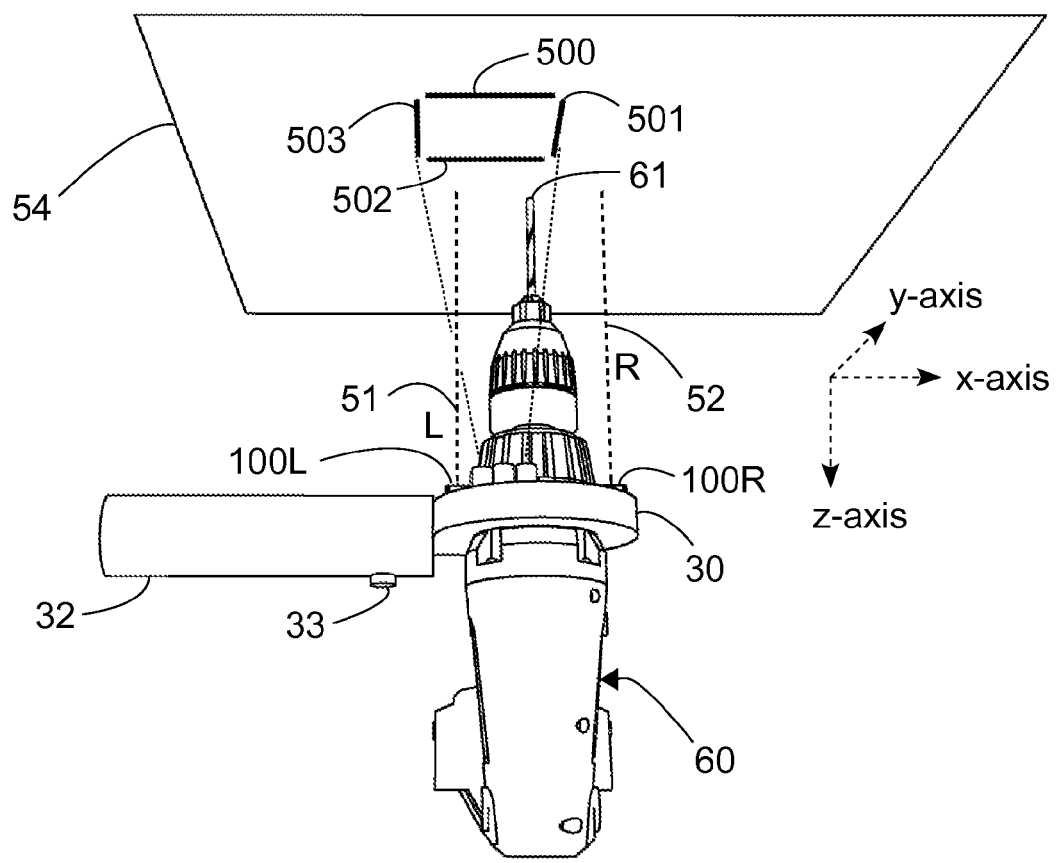
FIG. 2 shows a perspective top view of the first embodiment mounted on a hand-held power drill.
Figure 4:
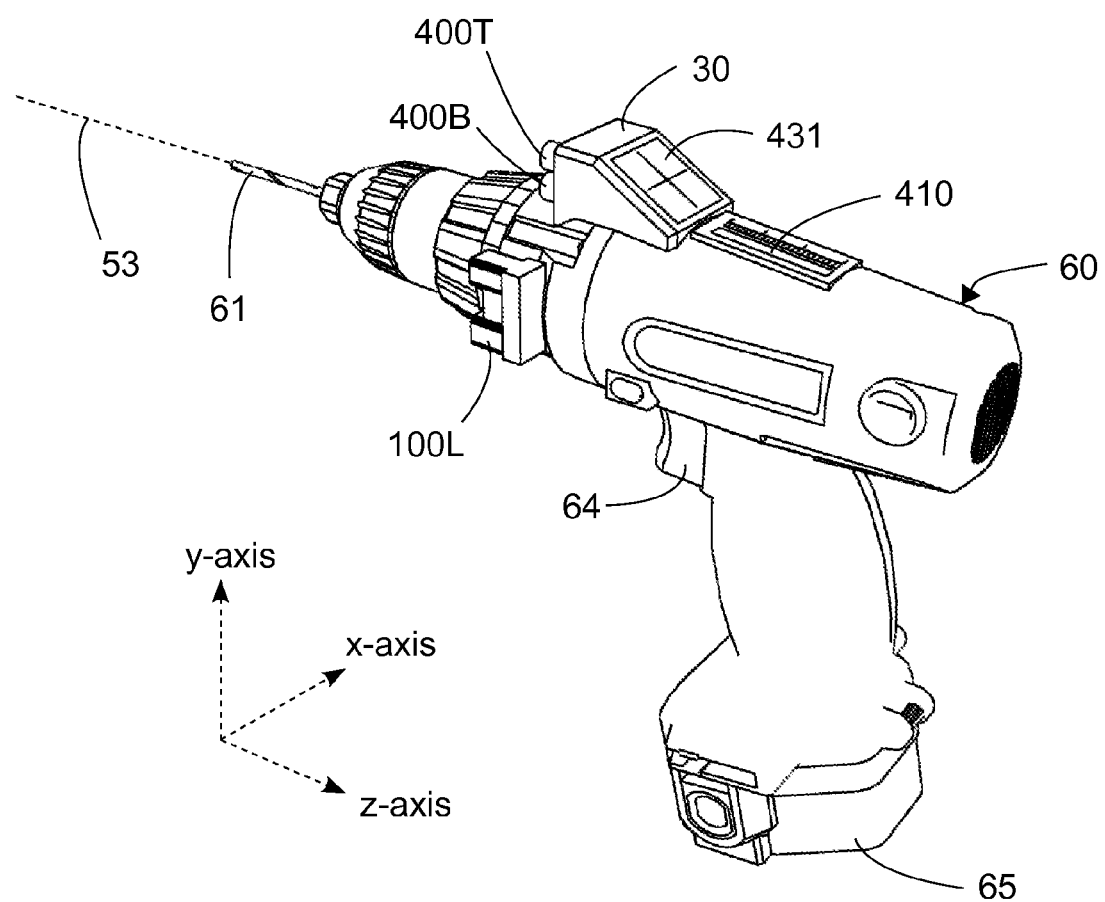
FIG. 4 shows a perspective side view of the embodiment of FIG. 3.

FIG. 1 shows a perspective front view of the electronic drill guide constructed in accordance with one embodiment. This embodiment is in the form of an auxiliary handle for a power drill. An enclosure 30 has an opened collar 40 which fits around the neck of a power drill. The collar 40 has a gap 31. A handle 32 is connected to a threaded bolt 34 which is threaded into the enclosure 30 such that twisting the handle 32 tightens or loosens the collar 40. Batteries (not shown) are contained within the handle 32. Referring to FIG. 2 and FIG. 4, the power drill 60 has a drill bit 61 which rotates about a working axis or drilling axis 53. The base of the drill 60 has a battery pack 65. The enclosure 30 has a front plane which is perpendicular to the drilling axis 53 of the power drill when the enclosure 30 is mounted to the drill 60. Referring to FIG. 1, distance sensor modules 100R, 100L are mounted, facing forward, to the front plane of the enclosure 30. Distance sensor 100R is positioned a predetermined distance to the right (from the perspective of the drill operator) of the center of the collar 40. Similarly, distance sensor 100L is positioned an equal distance to the left of the center of the collar 40. In some embodiments, the distance sensor modules 100R, 100L are for example but not limited to GP2Y0A02YK0F produced by Sharp Corporation. A display mechanism comprising forward-facing laser projectors 400R, 400L, 400T, 400B is mounted to the enclosure 30.

FIG. 2 shows a perspective top view of the embodiment of FIG. 1 mounted on a power drill 60. A push button switch 33 is mounted to the handle 32 at a location where it may be depressed by the operator. The switch 33 is wired in series with the batteries. The projectors 400R, 400L, 400T, 400B are individually aimed such that a predetermined light pattern or graphic symbol is formed on a target surface 54 when they are activated individually or in combination. Referring to FIG. 2 and FIG. 12E, projector 400T produces a symbol element 500, projector 400R produces a symbol element 501, projector 400B produces a symbol element 502, and projector 400L produces a symbol element 503.

Figure 7:
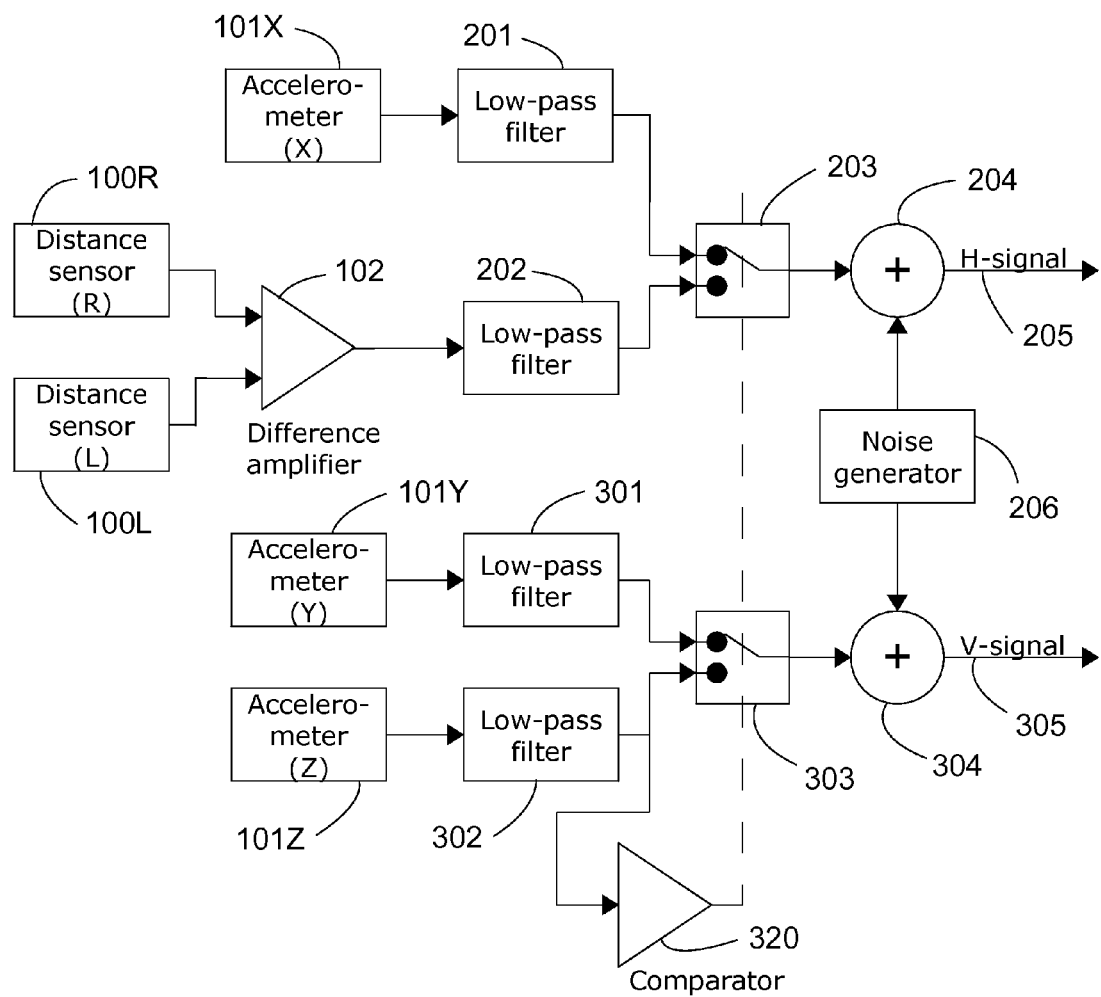
FIG. 7 is a block diagram of the front-end electronics of one embodiment of the electronic drill guide in "floor" mode.
Figure 7:
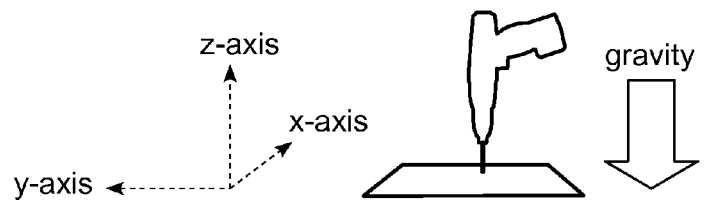
Figure 8:
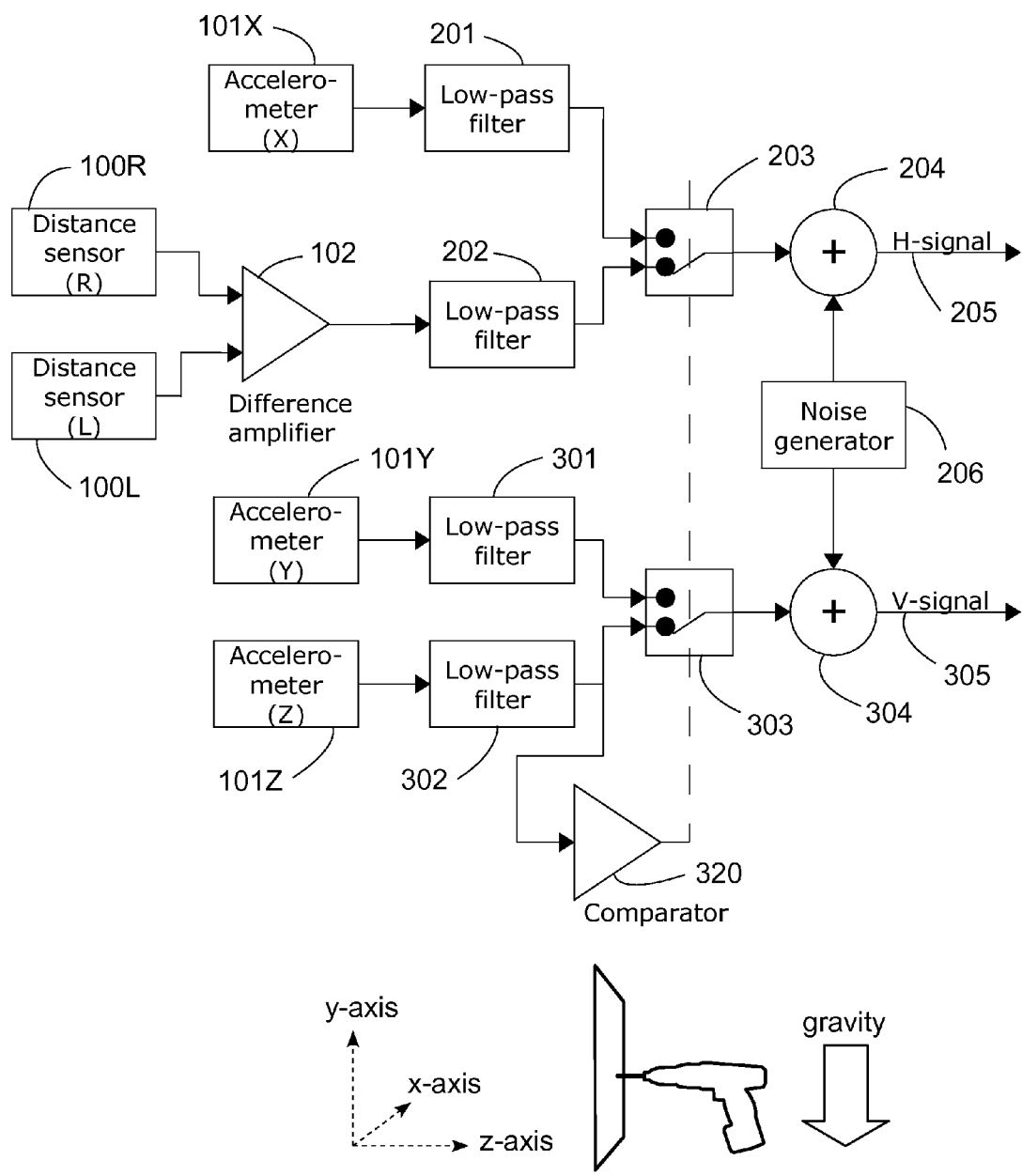
FIG. 8 is a block diagram of the front-end electronics of one embodiment of the electronic drill guide in "wall" mode.
Figure 9:
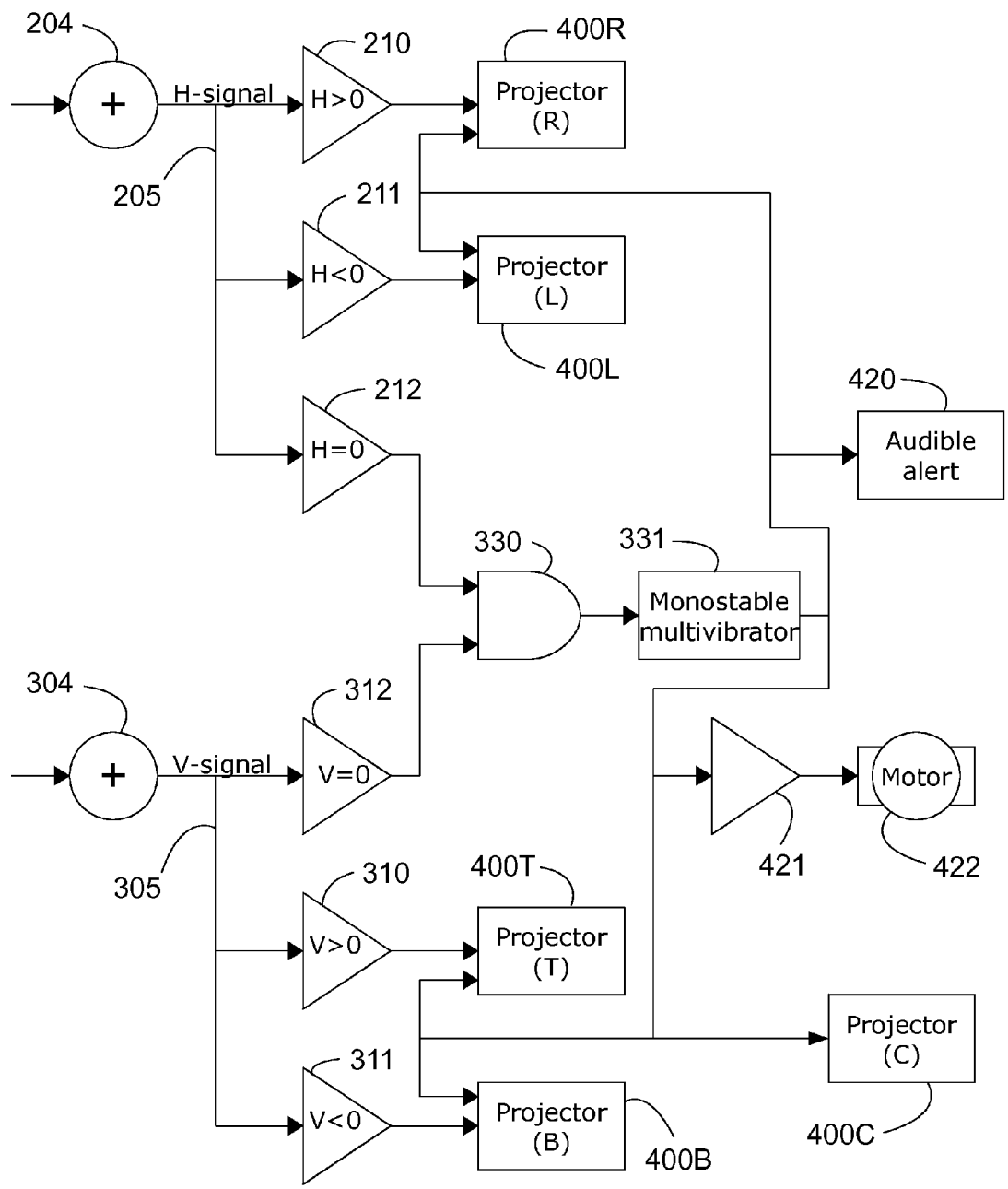
FIG. 9 is a block diagram of the back-end electronics of one embodiment of the electronic drill guide.

FIGS. 7, 8, and 9 are block diagrams of the electronics of one embodiment. Electronic components or electronics performing functions represented by the block diagram are mounted on a printed circuit board (not shown) contained within the enclosure 30. The batteries contained within the handle 32 supply power to the electronics.

Referring to FIG. 7, distance sensor 100R with an analog output voltage corresponding to distance measurements is connected to a non-inverting input of a difference amplifier circuit 102. Distance sensor 100L with an analog output voltage corresponding to distance measurements is connected to an inverting input of the difference amplifier 102. An analog switch 203 has a first input, a second input, a control input, and an output. The difference amplifier 102 has its output filtered with a low-pass filter 202 before connecting to the first input of analog switch 203. A three-axis accelerometer 101X, 101Y, 101Z is mounted on the printed circuit board (not shown) such that the x-axis runs horizontally left to right from the perspective of the drill operator, the y-axis runs vertically down to up from the perspective of the drill operator, and the z-axis runs parallel to the drilling axis 53 of the drill 60. The three axes are orthogonal to each other. In some embodiments, the accelerometer modules are for example but not limited to MMA7361L, a three-axis low-g micromachined accelerometer with analog outputs produced by Freescale Semiconductor. The three-axis accelerometer 101X, 101Y, 101Z has an x-axis output, a y-axis output, and a z-axis output. The (x-axis) output of accelerometer 101X is filtered with a low-pass filter 201 before connecting to the second input of analog switch 203. The switching action of the analog switch 203 is controlled by a comparator 320 which is connected to the control input of analog switch 203. A summing circuit or summer 204 has a first input, a second input, and an output. The analog switch's 203 output is connected to the first input of summer 204. A noise generator 206 is connected to the second input of summer 204. The output of summer 204 is referred to as the H-signal 205.

Referring to FIG. 9, comparator circuits 210, 211, 212 have inputs and outputs. The H-signal 205 is fed into the three comparator circuits 210, 211, 212. The reference level inputs for the comparators 210, 211, 212 are predetermined such that their behavior is as follows: The output of comparator 210 is an active-high if the H-signal 205 is positive or greater than zero. The output of comparator 211 is an active-high if the H-signal 205 is negative or less than zero. The output of window comparator 212 is an active-high if the H-signal 205 is equal to zero. The output of comparator 210 controls projector 400R. The output of comparator 211 controls projector 400L. An AND gate 330 has a first input, a second input and an output. The output of window comparator 212 is fed into the first input of AND gate 330. The output of AND gate 330 triggers a retriggerable monostable multivibrator 331. The monostable multivibrator 331 activates an audible alerting device or audible alert 420 and a motor driver 421. The motor driver 421 powers a vibrator motor 422. The vibrator motor 422 forms part of a mechanical vibration alerting device or mechanical vibrator. The audible alert 420 utilizes a piezoelectric-type audio transducer which produces a momentary audible tone.

Referring to FIG. 7, an analog switch 303 has a first input, a second input, a control input, and an output. The (y-axis) output of accelerometer 101Y is filtered with a low-pass filter 301 and then connected to the first input of the analog switch 303. The (z-axis) output of accelerometer 101Z is filtered with a low-pass filter 302 before being fed to the second input of the analog switch 303 and also an input of a comparator 320. The output of comparator 320 is connected to the control input of analog switch 303 which controls the switching action of analog switch 303. A summing circuit or summer 304 has a first input, a second input, and an output. The output of analog switch 303 is connected to the first input of summer 304. The noise generator 206 is connected to the second input of summer 304. The output of summer 304 is referred to as the V-signal 305.

Referring to FIG. 9, comparator circuits 310, 311, 312 have inputs and outputs. The V-signal 305 is fed into the three comparator circuits 310, 311, 312. The reference level inputs for the comparators 310, 311, 312 are predetermined such that their behavior is as follows: The output of comparator 310 is an active-high if the V-signal 305 is positive or greater than zero. The output of comparator 311 is an active-high if the V-signal 305 is negative or less than zero. The output of window comparator 312 is an active-high if the V-signal 305 is equal to zero. The output of comparator 310 controls projector 400T. The output of comparator 311 controls projector 400B. The output of window comparator 312 is fed into the second input of AND gate 330.

OPERATION

First Embodiment—FIGS. 1, 2, 7-9, 12A-J, 13A-J

Referring to FIG. 2, the drill operator attaches the first embodiment to a power drill 60 in a manner similar to attaching an auxiliary handle to a standard hammer drill. The drill 60 is positioned in front of the target surface 54 to be drilled. The drill operator depresses the latching switch 33 to activate the electronic drill guide. In some embodiments, the switch 33 may be a momentary switch which activates the electronics for a predetermined time. Upon activation, (z-axis) accelerometer 101Z is used to determine the general orientation of the drill 60 by measuring the relative direction of the acceleration due to gravity of the Earth. Depending on the general orientation of the drill 60, the drill guide will be forced into one of two modes: a "floor" mode or a "wall" mode. For the following description, we will assume the existence of a level floor surface which is perpendicular to the direction of acceleration due to gravity and a wall surface which is perpendicular to the floor. We will also assume that the drill operator is facing the rear of the drill 60 and that the drill operator is holding the drill 60 normally with the battery pack 65 of the drill 60 pointed substantially down when drilling into the wall or pointed towards his or her body when drilling into the floor. The term "floor" is chosen for ease of explanation and is not intended to limit the use of the embodiment exclusively to horizontal surfaces positioned lower relative to the drill operator.

Referring to FIG. 7, accelerometer 101Z measures acceleration in the z-axis which is parallel to the drilling axis 53 of the drill 60. If the drill 60 is pointed substantially down, towards the center of the Earth, the acceleration measured in the z-axis will be close to −1 g. If the drill 60 is pointed substantially towards the horizon of the Earth, the acceleration measured in the z-axis will be close to 0 g. Comparator 320 compares the output of accelerometer 101Z with a predetermined threshold. Comparator 320 controls analog switch 203 and analog switch 303. If the drill 60 is pointed substantially down (towards the floor), "floor" mode is active and as a result, the (x-axis) accelerometer 101X and (y-axis) accelerometer 101Y will be selected by analog switch 203 and analog switch 303 to determine the precise drill 60 orientation. FIG. 7 shows a representation of the switch position of the analog switches 203, 303 in "floor" mode. If the drill 60 is pointed substantially horizontally (towards the wall), "wall" mode is active and the (z-axis) accelerometer 101Z and distance sensors 100R, 100L will be used to determine the precise drill 60 orientation. FIG. 8 shows a representation of the switch position of the analog switches 203, 303 in "wall" mode.

Referring to FIG. 7, "floor" mode operation is explained as follows: Assume that the drill operator is facing the rear of the drill 60 and that the drill operator is holding the drill 60 normally such that the drill 60 is pointed vertically in the general direction of the floor and the battery pack 65 is pointed substantially towards his or her body. Since the drill 60 is pointed vertically in the general direction of the floor, the embodiment uses (x-axis) accelerometer 101X and (y-axis) accelerometer 101Y to determine whether or not the drill 60 is perpendicular to the floor. The output of accelerometer 101X should be zero if the x-axis of the drill 60 is level or parallel to the floor. Similarly, the output of accelerometer 101Y should be zero if the y-axis of the drill 60 is level or parallel to the floor. If the x-axis and y-axis of the drill 60 are both parallel to the floor, it follows that the drilling axis 53 is perpendicular to the floor.

The output of (x-axis) accelerometer 101X is filtered by low-pass filter 201 in order to reduce unwanted signals due to vibration. The filtered accelerometer 101X output is passed through analog switch 203 and fed to summing circuit or summer 204 where it is combined with a controlled noise source produced by noise generator 206. The noise generator 206 produces a predetermined amount of voltage noise which is small in comparison with the filtered sensor output levels. The filtered accelerometer 101X output combined with noise is referred to as the H-signal 205.

Referring to FIG. 9, the H-signal 205 is fed into comparator 210, comparator 211 and window comparator 212. When the drill 60 is pointed down and the x-axis of the drill 60 is parallel to the floor (x-axis perpendicular to the direction of the acceleration due to gravity), the H-signal 205 is zero and as a result, window comparator 212 is active. If the drill 60 is oriented perpendicular to the floor and then pointed slightly to the left (in the negative x-axis direction) of its perpendicular orientation, the H-signal 205 becomes slightly negative and as a result, comparator 211 becomes active. When comparator 211 is active, projector 400L is turned on, projecting the symbol element 503 shown in FIG. 2 onto the target surface 54 or floor. If the drill 60 is oriented perpendicular to the floor and then pointed slightly to the right of its perpendicular orientation, the H-signal 205 becomes slightly positive and as a result, comparator 210 becomes active. When comparator 210 is active, projector 400R is turned on, projecting the symbol element 501 shown in FIG. 2 onto the target surface 54 or floor.

Refer to FIG. 7. Similarly, the output of (y-axis) accelerometer 101Y is filtered by low-pass filter 301 in order to reduce unwanted signals due to vibration. The filtered accelerometer 101Y output is passed through analog switch 303 and fed to summing circuit or summer 304 where it is combined with the voltage noise produced by noise generator 206. The filtered accelerometer 101Y output combined with noise is referred to as the V-signal 305.

Referring to FIG. 9, the V-signal 305 is fed into comparator 310, comparator 311 and window comparator 312. When the drill 60 is facing the floor and the y-axis of the drill 60 is parallel to the floor (y-axis perpendicular to the direction of the acceleration due to gravity), the V-signal 305 is zero and as a result, window comparator 312 is active. If the drill 60 is oriented perpendicular to the floor and then pointed slightly down (in the negative y-axis direction) from its perpendicular orientation, the V-signal 305 becomes slightly negative and as a result, comparator 311 becomes active. When comparator 311 is active, projector 400B is turned on, projecting the symbol element 502 shown in FIG. 2 onto the target surface 54 or floor. If the drill 60 is oriented perpendicular to the floor and then pointed slightly up from its perpendicular orientation, the V-signal 305 becomes slightly positive and as a result, comparator 310 becomes active. When comparator 310 is active, projector 400T is turned on, projecting the symbol element 500 shown in FIG. 2 onto the target surface 54 or floor.

When the drill 60 is pointed down and its drilling axis 53 is perpendicular to the floor, the x-axis and y-axis will both be parallel to the floor. As a result, the output of (x-axis) accelerometer 101X and (y-axis) accelerometer 101Y will be zero (plus a small controlled amount of voltage noise) and both window comparator 212 and window comparator 312 will be active. Both window comparators 212, 312 have lower and upper setpoint levels which define their "window" of operation. An input signal between these setpoints activates the comparator. The lower and upper setpoints are predefined to be slightly below zero and slightly above zero, respectively. When H-signal 205 and V-signal 305 are simultaneously zero for a predetermined period of time, retriggerable monostable multivibrator 331 is triggered by AND gate 330. The monostable multivibrator 331 acts as a pulse stretcher, extending the duration of a brief trigger event. When monostable multivibrator 331 is triggered, all four projectors 400R, 400L, 400T, 400B, the audible alert 420, and the motor driver 421 are activated for a predetermined period of time. The motor driver 421 powers the vibrator motor 422. Thus, when the drill 60 is perpendicular to the floor, the drill operator is alerted via three types of feedback: visual feedback from the projected symbol shown in FIG. 2, audible feedback in the form of an audible alert and tactile feedback in the form of vibration.

Referring to FIG. 8, "wall" mode operation is explained as follows: Assume that the drill operator is facing the rear of the drill 60 and that the drill operator is holding the drill 60 normally such that the drill 60 is pointed horizontally in the general direction of the wall and the battery pack 65 is pointed substantially down towards the floor. Since the drill 60 is now pointed horizontally in the general direction towards the wall, the embodiment uses (z-axis) accelerometer 101Z and distance sensors 100L, 100R to determine whether or not the drill 60 is perpendicular to the wall. Accelerometer 101Z is used to determine if the drill 60 is parallel to the wall along the y-axis. Distance sensors 100L, 100R are used to determine if the drill 60 is parallel to the wall along the x-axis. If the x-axis and y-axis of the drill 60 are both parallel to the wall, it follows that the drilling axis 53 is perpendicular to the wall.

Distance sensor 100L measures the distance between itself and the wall along a line parallel to the drilling axis 53. Referring to FIG. 2, this measurement is illustrated as distance "L" 51 and the wall is represented by target surface 54. Similarly, distance sensor 100R measures the distance between itself and the target surface 54 along a line parallel to the drilling axis 53. This measurement is illustrated as distance "R" 52. When distance "L" 51 is equal to distance "R" 52, the x-axis of the drill guide is considered to be parallel to the target surface 54. Note that the distance sensors can be inexpensive non-linear types where the output voltage is not linearly proportional to the measured distance.

Referring to FIG. 2 and FIG. 8, difference amplifier 102 amplifies the difference between the output of distance sensor 100L and the output of distance sensor 100R. When the "L" distance 51 is equal to the "R" distance 52, the output of difference amplifier 102 is zero and the x-axis of the drill 60 is considered to be parallel to the target surface 54. If the drill 60 is pointed slightly to the right (in the positive x-axis direction), the "R" distance 52 will be greater than the "L" distance 51 and the output of difference amplifier 102 will be positive. Conversely, if the drill 60 is pointed slightly to the left, the "L" distance 51 will be greater than the "R" distance 52 and the output of difference amplifier 102 will be negative. The output of difference amplifier 102 is filtered by low-pass filter 202 in order to reduce errors due to sensor noise. The filtered difference amplifier 102 output is passed through analog switch 203 and fed to summing circuit or summer 204 where it is combined with the controlled noise source produced by noise generator 206. The filtered difference amplifier 102 output combined with noise is referred to as the H-signal 205.

Referring to FIG. 2 and FIG. 9, the H-signal 205 is fed into comparator 210, comparator 211 and window comparator 212. When the drill 60 is pointed horizontally at the wall such that distance sensor 100L and distance sensor 100R are the same distance from the wall, the H-signal 205 is zero and as a result, window comparator 212 is active. If the drill 60 is oriented perpendicular to the wall and then pointed slightly to the left (in the negative x-axis direction) of its perpendicular orientation, the H-signal 205 becomes slightly negative because the "L" distance 51 is greater than the "R" distance 52 and as a result, comparator 211 becomes active. When comparator 211 is active, projector 400L is turned on, projecting the symbol element 503 shown in FIG. 2 onto the target surface 54 or wall. If the drill 60 is oriented perpendicular to the wall and then pointed slightly to the right of its perpendicular orientation, the H-signal 205 becomes slightly positive because the "L" distance 51 is less than the "R" distance 52 and as a result, comparator 210 becomes active. When comparator 210 is active, projector 400R is turned on, projecting the symbol element 501 shown in FIG. 2 onto the target surface 54 or wall.

Referring to FIG. 8, the output of (z-axis) accelerometer 101Z is filtered by low-pass filter 302 in order to reduce unwanted signals due to vibration. The filtered accelerometer 101Z output is passed through analog switch 303 and fed to summing circuit or summer 304 where it is combined with the controlled noise source produced by noise generator 206. The filtered accelerometer 101Z output combined with noise is referred to as the V-signal 305. Referring to FIG. 9, the V-signal 305 is fed into comparator 310, comparator 311 and window comparator 312.

When the drill 60 is pointed horizontally at the wall such that the drilling axis 53 of the drill 60 is perpendicular to the wall, the z-axis is parallel to the floor (z-axis perpendicular to the direction of the acceleration due to gravity) which means the output of (z-axis) accelerometer 101Z will be zero. This makes the V-signal 305 zero and as a result, window comparator 312 is active. If the drill 60 is oriented perpendicular to the wall and then pointed down slightly (in the negative y-axis direction) from its perpendicular orientation, the V-signal 305 becomes slightly negative and as a result, comparator 311 becomes active. When comparator 311 is active, projector 400B is turned on, projecting the symbol element 502 shown in FIG. 2 onto the target surface 54 or wall. If the drill 60 is oriented perpendicular to the wall and then pointed up slightly from its perpendicular orientation, the V-signal 305 becomes slightly positive and as a result, comparator 310 becomes active. When comparator 310 is active, projector 400T is turned on, projecting the symbol element 500 shown in FIG. 2 onto the target surface 54 or wall.

When the drill 60 is pointed horizontally towards the wall and its drilling axis 53 is perpendicular to the wall, the z-axis will be parallel to the floor and the x-axis will be parallel to the wall. As a result, the H-signal 205 will be zero volts (plus a small controlled amount of voltage noise) because the output of difference amplifier 102 is zero. The V-signal 305 will also be zero volts (plus a small controlled amount of noise voltage) because the output of (z-axis) accelerometer 101Z is zero. Refer to FIG. 9. When H-signal 205 and V-signal 305 are simultaneously zero for a predetermined period of time, window comparator 212 and window comparator 312 cause the AND gate 330 to trigger monostable multivibrator 331. The retriggerable monostable multivibrator 331 acts as a pulse stretcher, extending the duration of a brief trigger event. When monostable multivibrator 331 is triggered, all four projectors 400R, 400L, 400T, 400B, the audible alert 420, and the motor driver 421 are activated for a predetermined period of time. The motor driver 421 powers the vibrator motor 422. Thus, when the drill 60 is perpendicular to the wall, the drill operator is alerted via three types of feedback: visual feedback from the projected symbol shown in FIG. 2, audible feedback in the form of an audible alert and tactile feedback in the form of vibration.

There are nine possible categories or states into which the drill 60 orientation relative to the target surface 54 can be classified. From the perspective of the drill operator, the drill 60 can be pointed: 1) to the upper left; 2) up; 3) to the upper right; 4) left; 5) straight or perpendicular to the target surface 54; 6) right; 7) to the lower left; 8) down; and 9) to the lower right. These nine states are mapped to the orientation symbols shown in FIGS. 12A, 12B, 12C, 12D, 12E, 12F, 12G, 12H, and 12J, respectively. In this embodiment, the orientation symbols are projected onto the target surface 54 using a projection display as shown in FIG. 2. In other embodiments, the orientation symbols are displayed on an integrated digital display. Symbol elements 500, 501, 502, 503, displayed individually or in combination, form each of the nine orientation symbols. In this embodiment, the projection display comprises symbol element projectors 400T, 400R, 400B, 400L which are standard line laser modules with a narrow fan angle, for example 20 degrees or less. Each laser module projects a visible line segment onto the target surface 54 directly in front of the laser module. The fan angle determines the length of the projected line segment at a given distance. Projector 400T produces symbol element 500, projector 400R produces symbol element 501, projector 400B produces symbol element 502, and projector 400L produces symbol element 503. The projectors 400T, 400R, 400B, 400L are mounted and aimed such that the orientation symbols shown in FIGS. 12A, 12B, 12C, 12D, 12E, 12F, 12G, 12H, and 12J can be displayed by activating the appropriate projectors in combination. Thus, the components numbered 201 to 331 constitute a means for mapping the sensor outputs to symbol elements.

Depending on the drill 60 orientation, the corresponding orientation symbol is projected on the target surface 54, informing the drill operator of the current orientation of the drill 60. At the threshold between any of the nine orientation states, the projected image will flicker between the relevant symbols because of the noise produced by the noise generator 206. As the drill 60 orientation transitions from an old state to a new state, the symbol representing the old state gradually fades away to be replaced by the symbol representing the new state which gradually flickers into view. If the drill 60 is held in the perpendicular orientation for the predetermined period of time required to trigger the monostable multivibrator 203, the symbol representing the perpendicular state (FIG. 12E) will be steadily displayed, without any flicker, for the predetermined period of time determined by monostable multivibrator 331. If the drill 60 position is maintained in the perpendicular orientation, the monostable multivibrator 203 will continue to be triggered repeatedly and the symbol in FIG. 12E will continue to be displayed without flickering.

With these nine orientation symbols, the drill operator is informed of when the drill 60 is perpendicular to the target surface 54 and if it is not perpendicular, the drill operator is informed of the current orientation relative to the desired perpendicular state so that he or she may make the necessary correction to the drill 60 position. As the drill operator repositions the drill 60 in order to achieve the perpendicular state, the fade-in and fade-out characteristic of the symbols during state transitions provides useful feedback to the drill operator, confirming to the drill operator that the desired orientation is being approached. The response of the projection display to drill operator movement is intuitive because its behavior is analogous to that of a bubble level mounted on the rear of the drill. For example, FIG. 12A with the active upper-left symbol elements 500, 503 is analogous to a circular type bubble level where the air bubble is forced to the upper-left.

The behavior of the orientation symbols is also similar to the action of an imaginary forward-facing flashlight mounted to the drill 60. For example, if the drill 60 is pointed slightly to the upper-right, the relevant upper-right symbol elements 500, 501 in FIG. 12C are illuminated as one would expect. This "flashlight" behavior is especially apparent in the alternate orientation symbol series shown in FIGS. 13A-13J used in some embodiments. This embodiment uses additional combinatorial logic (not shown) and pulse width modulators (not shown) between the comparators 210, 211, 212, 310, 311, 312 and the projectors 400R, 400L, 400T, 400B. Pulse width modulators are used to vary the brightness of the symbol elements 500, 501, 502, 503 by switching the projectors 400R, 400L, 400T, 400B on and off very quickly. Pulse width modulation is used to vary the element brightness between 100% (full) brightness and 50% (half) brightness, for example. In the orientation symbols shown in FIGS. 13A-13J, 100% brightness is represented by a solid line and 50% brightness is represented by a dashed line. The symbol shown in FIG. 13F shows symbol element 501 at 100% brightness and symbol elements 500, 502, 503 at 50% brightness. In this particular symbol series, a square graphic symbol composed of four elements 500, 501, 502, 503 is projected onto the target surface 54 and as the drill operator varies the drill 60 orientation, the square's edges vary in brightness in accordance with the drill operator's movements. The line pattern forming the square is static but the line brightness varies. The dimmed elements help prevent any misinterpretation of the symbols which might occur if the dimmed elements were not visible. For example, if the dimmed elements were dimmed so much that they were rendered invisible, the symbols representing left (FIG. 13D) and right (FIG. 13F) would become ambiguous because they are both a single vertical line.

The orientation symbol design and response to the drill operator's actions makes the drill guide intuitive and easy-to-use. Furthermore, the drill operator never needs to look away from the target surface 54 to determine drill 60 orientation because the symbols are projected directly onto the target surface 54.

DESCRIPTION

Figure 3:
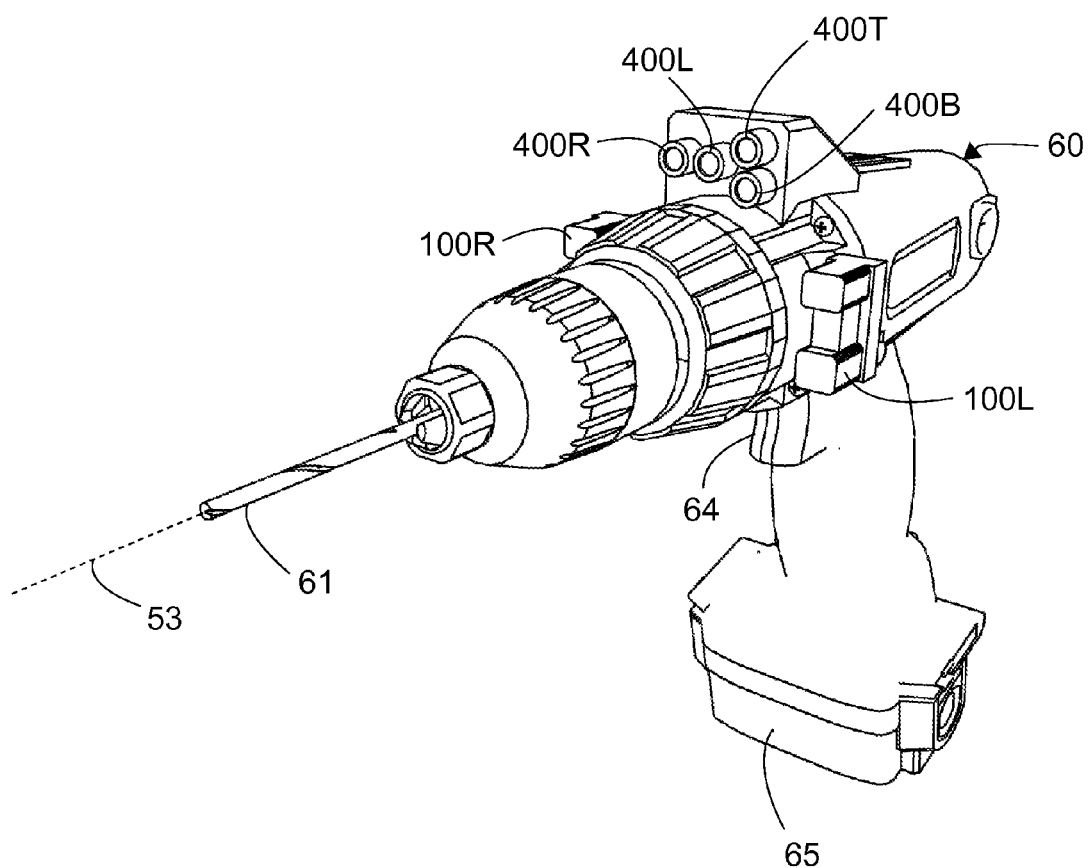
FIG. 3 shows a perspective front view of an additional embodiment of the electronic drill guide integrated into a power drill.

Additional Embodiments—FIGS. 3, 4

FIG. 3 shows a perspective front view of an additional embodiment of the electronic drill guide integrated into the enclosure of a power drill 60. An enclosure 30 is permanently fixed to the body of the drill 60 or it is a molded feature of the drill 60 enclosure. The drill 60 has a trigger 64 and a battery pack 65. Forward-facing laser projectors 400R, 400L, 400T, 400B are mounted to the enclosure 30. Distance sensors 100L, 100R are mounted, facing forward, on the left and right side of the drill 60. FIG. 4 shows a perspective side view of the embodiment of FIG. 3. The drill 60 has a bar-graph display 410 and a digital display 431.

OPERATION

Additional Embodiments—FIGS. 3, 4, 9-11

Figure 11:
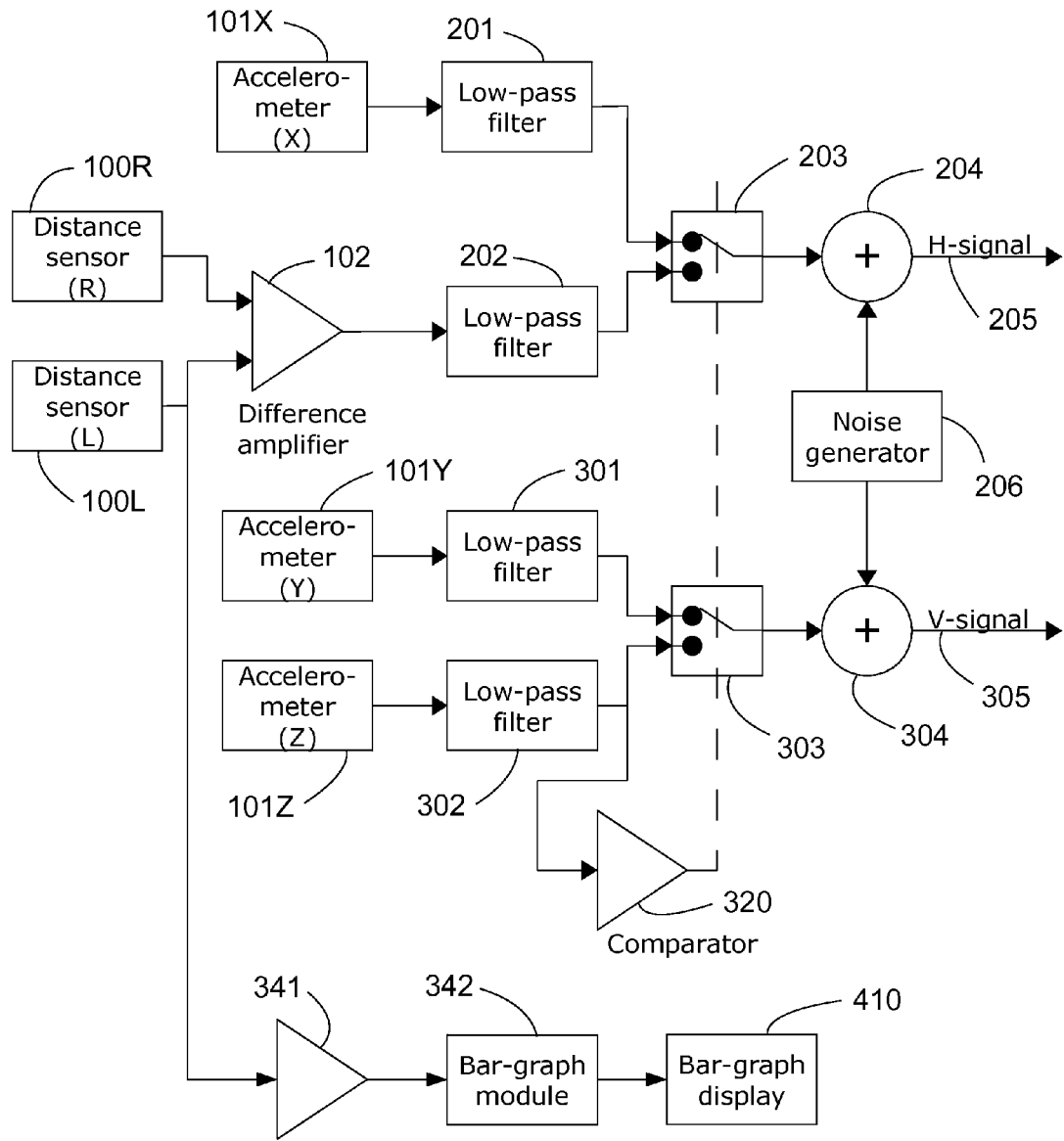
FIG. 11 is a block diagram of the front-end electronics of one embodiment of the electronic drill guide with a bar-graph display.

The operation of this embodiment is similar to that of the first embodiment. A partial depression of the trigger 64 activates the electronic drill guide circuitry. The power for the drill guide electronics is derived from the drill's battery pack 65. Referring to FIG. 11, an amplifier 341 of predetermined gain is connected to the analog output of distance sensor 100L. The amplifier 341 output is connected to a bar-graph module 342 which feeds bar-graph display 410. The bar-graph display 410 gives the drill operator a visual indication of the current drilling depth. The bar-graph module 342 senses an analog voltage level and drives a number of LEDs, providing a linear analog display. In some embodiments, the bar graph module 342 is for example but not limited to a LM3914 dot/bar display driver manufactured by Texas Instruments. The bar-graph display 410 has a graduated scale printed alongside. In some embodiments, the bar-graph display 410 is a liquid-crystal display (LCD). With the proper scaling and gain adjustments, each display segment could represent, for example, 0.25 inches. In some embodiments, the actual depth of the hole currently being drilled can be calculated and displayed because the distance to the target surface 54 at the start of drilling can be recorded and temporarily stored upon the initial depression of the trigger 64. The difference between the distance to the target surface 54 at the start of drilling and the current distance to the target surface 54 is the current depth of the hole.

Figure 10:
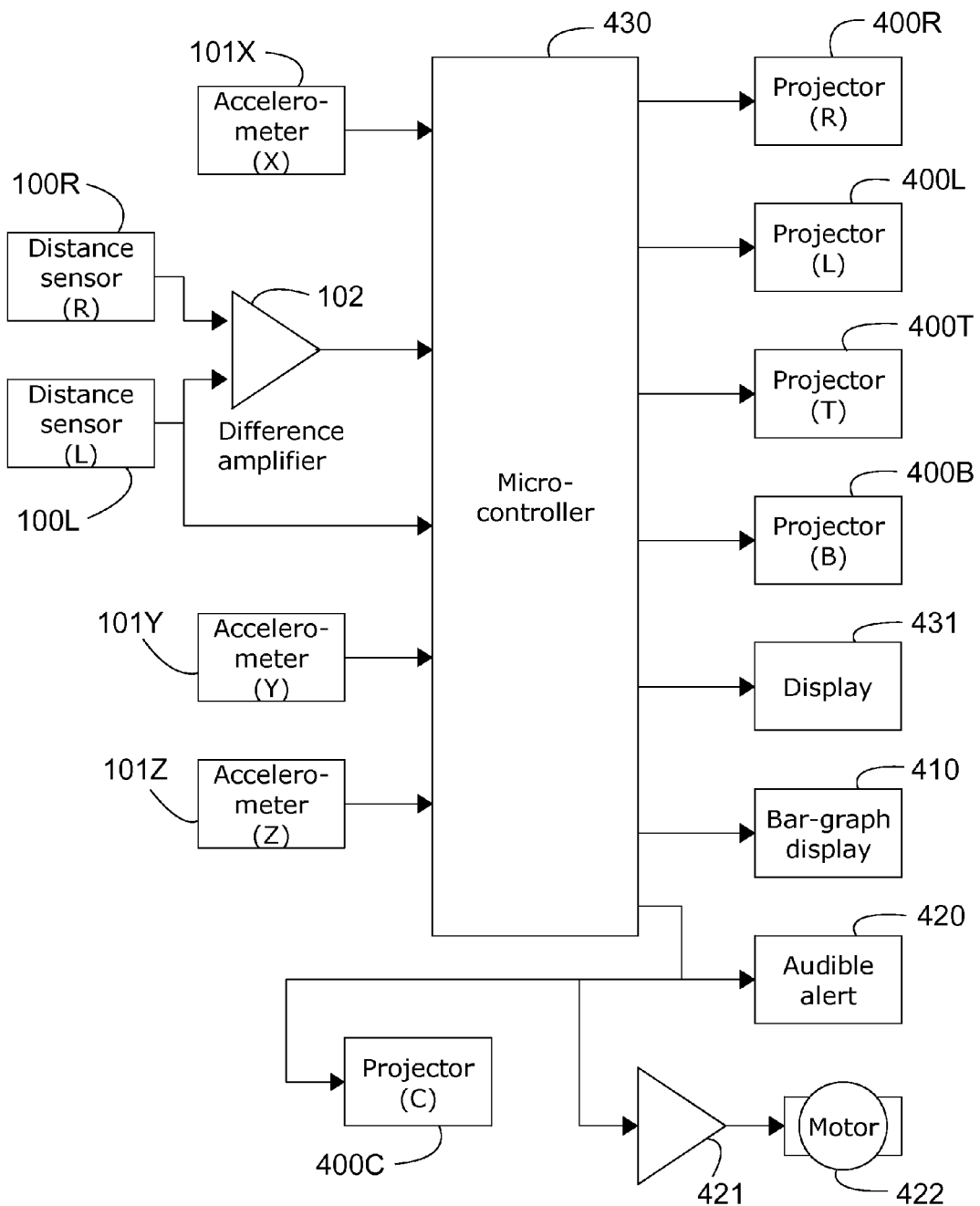
FIG. 10 is a block diagram of the electronics of a microcontroller-based embodiment of the electronic drill guide.

Any of the structural components of the electronic drill guide, e.g., the noise generator 206 and window comparator 212, may be implemented using commonly known hardware, such as one or more digital circuits, to perform the functions of the electronic drill guide. Alternatively, the functions of such structural components may be implemented using a dedicated signal processor, such as a microcontroller, that is programmed with instructions to perform the functions of the electronic drill guide. FIG. 10 is a block diagram of the electronics of a microcontroller-based embodiment.

Referring to FIG. 10, an x-y display can be created from a matrix of LEDs (light-emitting diode) controlled by a microcontroller with pre-programmed instructions for an x-y display function. This x-y display function is analogous to the x-y mode of a standard laboratory oscilloscope. A digital representation or equivalent of the H-signal 205 is fed into the x-axis input of the x-y display function and a digital equivalent of the V-signal 305 is fed into the y-axis input of the x-y display function. An LED dot representing the drill 60 orientation is visible on a digital matrix display 431. The dot's position is driven by the value of the digital equivalents of the H-signal 205 and the V-signal 305. When the drill 60 is in a perpendicular orientation, the dot is centered in the display 431. The behavior of the dot is similar to that of a bubble level. In some embodiments, the digital matrix display 431 is a liquid-crystal display (LCD).

In some embodiments, a fifth projector may be used to project a very distinctive symbol when the perpendicular orientation has been achieved. This fifth projector 400C is shown in FIG. 9. This distinctive symbol could be a symbol of a different graphic design, color, or intensity. For example, a different graphic design such as a bull's eye, a different color such as green, or a very bright attention-getting symbol.

In some embodiments, the display 431 is a simple LED or LCD (liquid-crystal display) digital display where individually addressable elements are arranged to form the symbols illustrated in FIGS. 12A-15J. In some embodiments, this digital display 431 is used in addition to the projection display. In other embodiments, this digital display 431 is used in place of the projection display.

In some embodiments, the display mechanism comprises an image projector capable of creating binary light patterns. A projection display module, for example but not limited to the DLP 1700 (Pico Projector 2.0) manufactured by Texas Instruments, could be used to project sophisticated information such as x-y data and drilling depth data onto the target surface 54. The projection display module would replace projectors 400R, 400L, 400T, 400B, 400C and bar-graph display 410.

DESCRIPTION

Alternative Embodiments—FIGS. 5, 6, 14, 15

Figure 5:
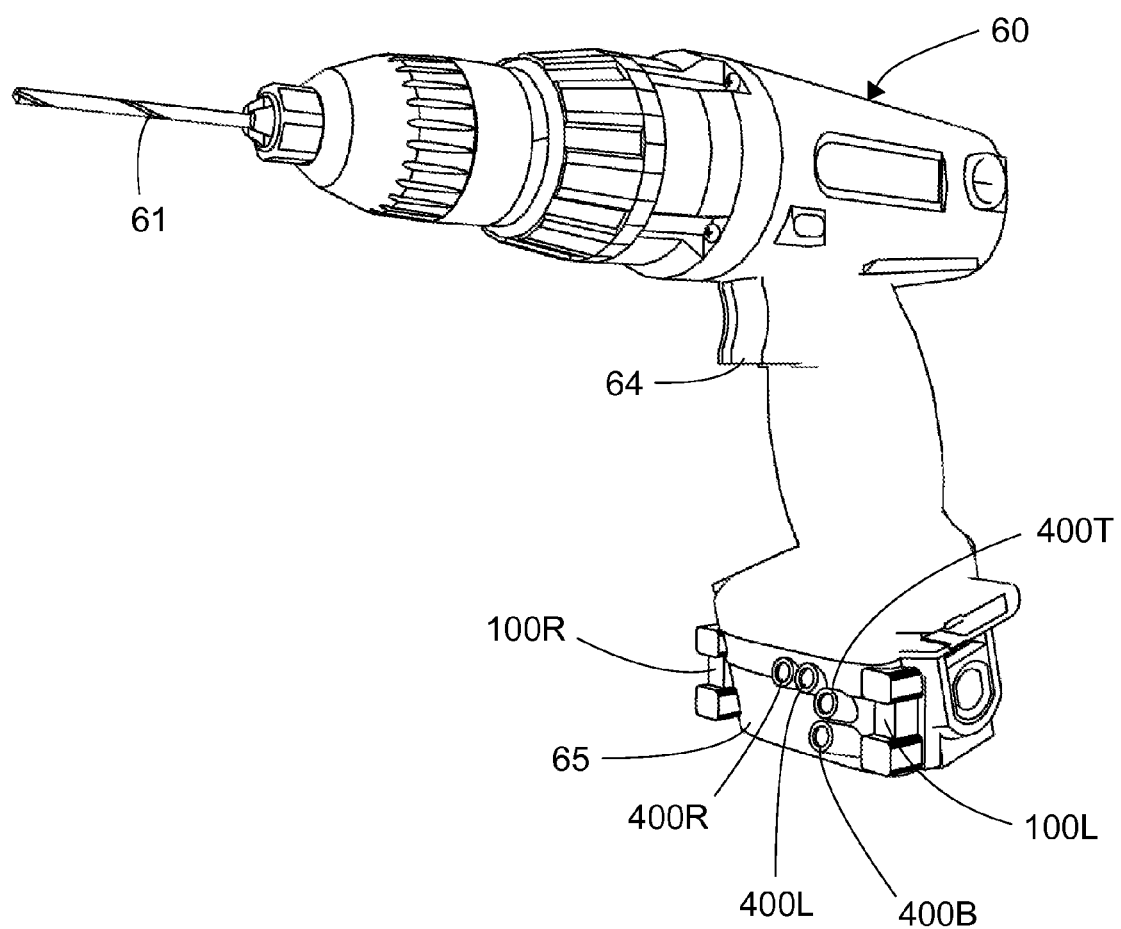
FIG. 5 shows a perspective front view of an alternate embodiment of the electronic drill guide integrated into the battery pack of a power drill.

FIG. 5 shows a perspective front view of the electronic drill guide constructed in accordance with an alternative embodiment. This embodiment is integrated into a power tool battery pack. The base of the drill 60 has a battery pack 65. Forward-facing laser projectors 400R, 400L, 400T, 400B are mounted to the battery pack 65. Distance sensors 100L, 100R are mounted, facing forward, on the left and right side of the battery pack 65.

The operation of this embodiment is similar to the first embodiment. The power for the drill guide electronics is derived from the drill's battery pack 65. Current-sensing circuitry (not shown) is added to the drill guide system such that when the drill 60 is briefly activated, the electronic drill guide is activated for a predetermined time. In some embodiments, the laser projectors 400R, 400L, 400T, 400B can be fixed, as a group, to a swiveling mount so that the drill operator can move the location of the projected orientation symbols to a convenient area on the target surface 54.

Figure 6:
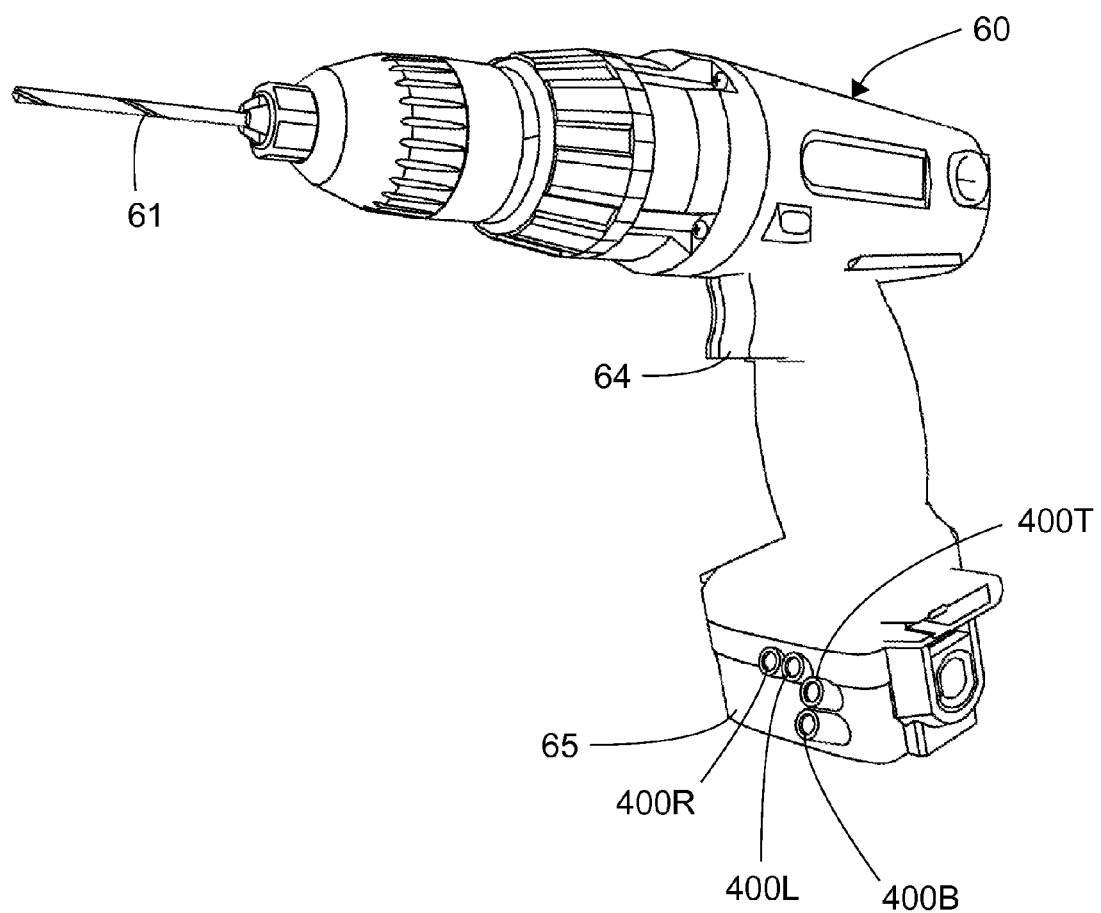
FIG. 6 shows a perspective front view of an another embodiment of the electronic drill guide integrated into the battery pack of a power drill.

FIG. 6 shows a perspective front view of the electronic drill guide constructed in accordance with another alternative embodiment. The embodiment shown in FIG. 6 is similar to the embodiment in FIG. 5 except there are no distance sensors 100L, 100R. This particular embodiment lacks the ability to measure distances to the target surface 54 and therefore when dealing with a vertical target surface, it can only detect the inclination. It lacks some capability but I believe it may be commercially viable for the following reasons: 1) By eliminating the most expensive components, the distance sensors 100L, 100R, it can be manufactured at very little cost; 2) A particular manufacturer's battery pack 65 typically fits many power drill models so this embodiment would be immediately usable on many drill models particularly those which cannot accept an auxiliary handle.

Some embodiments use the orientation symbol series shown in FIGS. 14A-14J. This variation of the series shown in FIGS. 12A-12J is achieved by rotating each of the projectors 400R, 400L, 400T, 400B by 90 degrees, essentially changing all vertical lines of FIGS. 12A-12J into horizontal lines and vice versa. The symbol series in FIGS. 15A-15J is used in another embodiment which utilizes laser projection modules outfitted with diffraction grating lenses. The diffraction grating lens converts a basic projected laser dot into a predefined image. A large variety of predefined images are commercially available. In this embodiment, the predefined image is the outline of an arrow. The arrow symbols indicate the direction in which the rear of the drill 60 should be tipped in order to achieve the desired perpendicular orientation.

In some embodiments, the symbols representing diagonal orientations, eg. upper-left, upper-right, lower-left, and lower-right, can be obtained by multiplexing or switching quickly between displaying two primary symbols, the primary symbols being the symbols for: up, down, left, and right. For example, the "upper-left" symbol (FIG. 15A) can be obtained by switching quickly between the "up" symbol (FIG. 15B) and the "left" symbol (FIG. 15D). The drill operator sees the combined symbol because of persistence of vision. Similarly, the symbol representing "perpendicular" (FIG. 15E) can be achieved by multiplexing all four primary symbols. Thus, the nine symbols used to identify orientation can be obtained using only four primary symbols where only one symbol element is active at any given time.

CONCLUSION, RAMIFICATIONS, AND SCOPE

Thus the reader will see that at least one embodiment of the electronic drill guide provides an effective non-contact method and system for determining the orientation of a power drill relative to a surface, especially a vertical surface.

While my above description contains many specificities, these should not be construed as limitations on the scope, but rather as an exemplification of several embodiments thereof. Many other variations are possible. For example, the embodiments shown here use an infrared light-based distance sensor 100L, 100R but any type of distance sensor could be used such as ultrasonic sound-based distance sensors or laser-based distance sensors.

The placement of the distance sensors 100L, 100R on the apparatus is somewhat flexible leading to many physicals variations. The main consideration when mounting the distance sensors 100L, 100R on the apparatus is that a substantial horizontal distance should exist between the two distance sensors 100L, 100R. Note that the distance sensors 100L, 100R do not need to be placed on opposite sides of the drilling axis 54. For example, an embodiment where both distance sensors 100L, 100R are mounted on the handle 32 (on the same side of the drilling axis 54) would work satisfactorily. Furthermore, the distance sensors 100L, 100R do not need to be on the same plane perpendicular to the z-axis, ie. they do not need to be mounted on the same front plane of the apparatus. Any offset in their position in the z-axis direction can be "zeroed-out" or corrected during the processing stage.

Some embodiments use a momentary switch, such as a trigger 64, to activate the drill guide electronics. These embodiments use a timer to automatically shut off the electronics after a predetermined time in order to conserve battery power. These embodiments could use the accelerometers 101X, 101Y, 101Z as a motion sensor, maintaining power as long as the tool experiences movement. Another power-saving measure used by some embodiments is to disconnect power to the distance sensors 100L, 100R when the guide is in "floor" mode since the distance sensors 100L, 100R are not needed unless the drilling depth bar-graph display 410 feature is implemented.

In some embodiments, at least one additional distance sensor, mounted non-collinearly relative to the main two distance sensors 100L, 100R, can be used to determine orientation relative to target surfaces 54 which are at arbitrary angles, ie. target surfaces 54 which are neither horizontal nor vertical. In this embodiment, if at least three distances measured by the distance sensors are equal, the drilling axis 53 is deemed to be perpendicular to the target surface 54.

In some embodiments, the projection modules 400R, 400L, 400T, 400B are standard line laser modules with a narrow fan angle, for example 20 degrees or less. A narrower fan angle is easily achieved by using a hood, similar to a lens hood for a standard camera lens, to block the unwanted laser light. In some embodiments, the laser modules are mounted directly onto a printed circuit board and the optical assembly is a single unit combining the function of four or more lenses or diffraction gratings.

In some embodiments, each projection module is basically a miniature slide projector where a bright visible light source, a lens, and an opaque stencil is used to control the pattern of light.

In some embodiments, the electronic drill guide is designed as a custom drill accessory where the drill guide enclosure is specially designed to mate with the drill enclosure. For example, the electronic drill guide could snap onto the top of the power drill enclosure.

Some embodiments may be used with power tools other than a power drill such as a nail gun. Other embodiments may be used to align objects such as a surveyor's sight rod.

From the above description, it can be easily understood that the advantages of some embodiments of the electronic drill guide are as follows:

(a) No mechanical jigs are required, increasing safety and convenience.

(b) The operator is able to use the drill guide to help position a drill truly perpendicular to a vertical target surface (the drilling axis is orthogonal to both the horizontal and vertical axis of the target surface).

(c) Unlike a bubble level, the device is easy to read since the drill orientation status is unambiguous and clearly projected directly onto the target surface. Furthermore, the drill operator does not need to look away from the target surface.

(d) The drill orientation symbols provide the drill operator with unambiguous notification of when the drill orientation is perpendicular to the target surface, allowing consistent and repeatable operation regardless of the tool operator's judgment or skill.

(e) Use of the electronic drill guide is intuitive because the behavior of the drill orientation symbols (used as feedback to help reposition the drill) is analogous to the behavior of familiar objects: a bubble level and a flashlight.

(f) The electronic drill guide is designed to use accelerometers instead of distance sensors wherever possible. A person having ordinary skill in the art knows that accelerometers are inherently more accurate and less expensive than distance sensors resulting in higher performance at less cost.

In view of the foregoing, it will be appreciated that the electronic drill guide overcomes the long-standing need for a non-contact method and system for determining the orientation of a power drill relative to a surface, especially a vertical surface. The drill guide may be embodied in other specific forms without departing from its spirit or essential characteristics. The described embodiments are to be considered in all respects only illustrative and not restrictive. The scope of the drill guide is, therefore, indicated by the appended claims rather by the foregoing description. All changes that fall within the meaning and range of equivalency of the claims are to be embraced within their scope.

I claim:

1. An apparatus for facilitating the alignment of a power tool substantially parallel or substantially orthogonal with respect to the Earth's gravity, comprising:
   a. an enclosure suitable for attachment to said power tool;
   b. at least three accelerometers fixed to said enclosure, said accelerometers being orthogonal to each other, said accelerometers having outputs;
   c. a processing circuit connected to said accelerometer outputs;
   d. a noise generator connected to said processing circuit; and
   e. a projection display connected to said processing circuit, said projection display comprising at least four addressable laser line projectors, whereby the orientation of said power tool with respect to the Earth's gravity may be deduced from viewing said projection display's output.

2. The apparatus of claim 1 further including:
   a. a first forward-facing distance sensor fixed to said enclosure, said first distance sensor having an output;
   b. a second forward-facing distance sensor fixed to said enclosure, said second distance sensor having an output, said distance sensors having a substantial horizontal space between them, said distance sensor outputs connected to said processing circuit, whereby the orientation of said power tool with respect to a substantially vertical target surface may be deduced from viewing said projection display's output.

3. The apparatus of claim 2 further including an audible alerting device.

4. The apparatus of claim 3 integrated into said power tool.

5. The apparatus of claim 2 integrated into said power tool.

6. The apparatus of claim 2 integrated into a power tool battery pack.

7. A method of displaying the orientation of a tool, said tool having a working axis, comprising:
   a. providing at least four forward-facing laser line projectors projecting a luminous polygon onto a target surface;
   b. providing sensors measuring said tool's surroundings;
   c. calculating a vertical difference signal from said sensors;
   d. calculating a horizontal difference signal from said sensors;
   e. adding a predetermined noise signal to said vertical difference signal;
   f. adding said predetermined noise signal to said horizontal difference signal;
   g. varying the intensity of the output of said line laser projectors based on the value of said vertical difference signal and the value of said horizontal difference signal, whereby said tool orientation relative to said target surface is described by the relative brightness of the sides of said luminous polygon projected onto said target surface, in particular, when said working axis is oriented substantially orthogonal to said target surface.

8. The method of claim 7 wherein said polygon is a square.

9. The method of claim 7 wherein said laser line projectors comprise two vertical laser line projectors and two horizontal laser line projectors.

10. The method of claim 7 wherein said sensors comprise a plurality of accelerometers.

11. The method of claim 7 wherein said sensors comprise a plurality of distance sensors.

* * * * *